United States Patent [19]

Hu et al.

[11] Patent Number: 4,731,496

[45] Date of Patent: Mar. 15, 1988

[54] PROCESS FOR THE HYDROGENATION OF BENZENE TO CYCLOHEXANE

[75] Inventors: Shao-Chueh Hu; I-Kai Wang; Jung-Chung Wu, all of Chia-Yi, Taiwan

[73] Assignee: Chinese Petroleum Corporation, Taipei, Taiwan

[21] Appl. No.: 889,280

[22] Filed: Jul. 25, 1986

[51] Int. Cl.$^4$ .............................................. C07C 5/10
[52] U.S. Cl. .................................................. 585/270
[58] Field of Search ........................................ 585/270

[56] References Cited

U.S. PATENT DOCUMENTS 4,160,745  7/1979  Murrell et al. ................... 585/270

Primary Examiner—Curtis R. Davis
Attorney, Agent, or Firm—Fleit, Jacobson, Cohn & Price

[57] ABSTRACT

The present invention relates to an improvement in a process for the conversion of benzene in gas-phase to cyclohexane under a suitable operation conditions by hydrogenation over a specific supported nickel catalyst located on a fixed bed reactor, the improvement comprising that the specific supported nickel catalyst is a nickel catalyst supported by a mixture of titanium dioxide and zirconium dioxide. The present invention also relates to the operation condition for the hydrogenation of benzene, the optimal components of the catalyst used, process for the preparation of said specific supported catalysts and the conditions for pretreatment.

6 Claims, No Drawings

PROCESS FOR THE HYDROGENATION OF BENZENE TO CYCLOHEXANE

DETAILED DESCRIPTION OF THE INVENTION

Cyclohexane was first obtained directly by fractional distillation of suitable crude gasoline cuts, with the purity being however only 85%. With further purification the product quality was improved to almost 98% as a result of the simultaneous isomerization of methylcyclopentane to cyclohexane as operated by Humble Oil, Shell, and Atlantic Richfield in USA. Because of the markedly increasing demand for cyclohexane as precursor in manufacture of nylon 6 and nylon 6.6, this amount covers only a minor part of the cyclohexane requirement. The main quantity (approx. 80-85%) is obtained from the hydrogenation of benzene.

Of the numerous variants for the hydrogenation of benzene, the older high pressure processes—employing sulfur resistant catalysts with the benzene feedstock (which generally contained sulfur)—are insignificant today. Newer processes with nickel or platinum metal catalysts require extremely pure benzene with less than 1 ppm sulfur in order that the catalysts are effective in the liquid phase under mild conditions (20-40 bar, 170°-230° C.). In the exothermic hydrogenation, meticulous heat removal and observation of an upper temperature limit of approx. 230° C. with exact residence times are imperative to prevent equilibration between cyclohexane and methylcyclopentane. In several prosesses, there is only 95% conversion in the first stage, complete hydrogenation occurring in the finishing reactor. By this means, residual amounts of benzene and methylcyclopentane can be reduced to less than 100 ppm.

Liquid-phase hydrogenation are operated in several commercial plants for example by Mitsubishi Chemical, Hydrocarbon-Sinclair, and IFP. In the IFP process, a Raney nickel catalyst is employed in a bubble column reactor at 200°-225° C. and 50 bar. The nickel suspension is circulated to improve heat removal, the benzene being completely hydrogenated in a coupled fixed-bed reactor. Recently, numerous gas-phase hydrogenations have been developed e.g. by Arco, DSM, Toray, Houndry, and UOP. The Hydrar-process (UOP) uses a series of three reactors with a Ni/support and a stepwise increasing temperature (400°-600° C.) at 30 bar. Despite higher reaction temperatures, the isomerization between cyclohexane and methylcyclopentane does not equilibrate due to the short residence times. In the Arco process a noble metal catalyst is used by which conversion of benzene is achieved.

Kinetic studies of gas-phase benzene hydrogenation over supported nickel, palladium or platinum catalysts have been reported by Meerten, Coenen, Nakano, Basset, Franco, Phillips and many other workers. However, there is no report on benzene hydrogenation over supported nickel catalysts where Ti-Zr mixed metal oxides are used as the supports.

The present invention relates to an improvement in the process for the conversion of benzene into cyclohexane by gas-phase hydrogenation over supported nickel catalyst, the improvement comprising that the mixed Ti-Zr metal oxides in place of conventional alumina or diatomaceous earth are used as the supports.

The process for the preparation of the supported catalyst of this application comprises the sequential steps of preparing respectively the solutions of titanium compound and of zirconium compound in the anhydrous ethanol solution wherein titanium compound and zirconium compound may be the corresponding chloride or organic compounds;

mixing said two solutions of metal compounds in anhydrous ethanol in an appropriate ratio and adding dropwise the resultant mixture to excess ammonia aqueous solution with rapid stirring thereby obtaining a white co-precipitate; washing said co-precipitate which has been collected by filtration, with deionized water; drying the washed co-precipitate at 100° C.;

calcining the dried product at a temperature above 450° C. for more than 2 hours whereby a product that is the support for the catalyst is obtained;

impregnating the surface of said support with an appropriate amount of a aqueous solution of nickel compound and drying at 100° C. wherein said nickel compound may be selected from nickel nitrate, nickel chloride or any nickel salts of organic acids;

reducing the resultant product with hydrogen at a temperature of more than 250° C. after being calcined at a temperature of 90° to 500° C. whereby a catalyst of the present invention used for the hydrogenation of benzene is obtained.

The invention will now be illustrated with reference to the following examples.

EXAMPLE 1

The effect of the temperature at which the supported catalyst is calcined on the activity of the supported catalyst An equimolar quantity of titanium n-butoxide [$Ti(OC_4H_9)_4$] and zirconium chloride ($ZnCl_4$) is dissolved respectively in an appropriate amount of anhydrous ethyl alcohol. After two ethyl alcohol solutions are mixed, the mixture is added dropwise to an excess of aqueous ammonia solution to obtain a white co-precipitate of titanium hydroxide with zirconium hydroxide. The co-precipitate is collected by filtration and then washed with de-ionized water until the solution is free of chloride ion. After being dried at 100° C. the co-precipitate is calcined in air at 500° C. for 2 hours to obtain the support of this example. 3.4 ml of 1.0M nickel nitrate solution is mixed well with the above support, the mixture is then dried at 90° C. whereby a supported catalyst which contains as 2wt% of nickel is obtained.

The above supported catalyst is crushed to form granules of 20-30 mesh in size. The granules thus obtained are divided into three equal portions which after being calcined respectively at 90° C., 300° C. and 500° C. for 2 hours, are respectively placed in a continuous fixed bed reactor and tested for their activities under the same conditions as follows:

| | |
|---|---|
| reduction temperature | 400° C. |
| reduction time | 2 hours |
| reaction temperature | 120° C. |
| reaction pressure | 8 atm |
| liquid hourly space velocity | 4 v/v/hr |
| $C_6H_6/H_2$ mole ratio | 1/6 |

The result of the test is summarized in table 1 which shows that in the pre-treatment the lower is the calcination temperature the better is the activity.

TABLE 1

The effect of the temperature at which the supported catalyst is calcined on the activity of 2% Ni/TiO$_2$—ZrO$_2$ (1/1,500° C.) catalyst

| calcination temperature, °C. | conversion, % |
|---|---|
| 500 | 13 |
| 300 | 19 |
| 90 | 35 |

EXAMPLE 2

Effect of reduction temperature on the catalytic activity

An equimolar solutions of titanium chloride (TiCl$_4$) and zirconium chloride (ZrCl$_4$) in anhydrous ethanol are mixed and treated with excess aqueous ammonia solution to obtain a co-precipitate of titanium hydroxide and zirconium hydroxide. After working up said co-precipitate in a manner similar in example 1 it is calcined at 500° C. to obtain a support which is then impregnated with an appropriate amount of aqueous nickel oxalate solution and dried at 90° C. so as to obtain a supported catalyst which contains 2% by weight of nickel catalyst. The supported catalyst is then divided into four equal portions which are all reduced in reactors with hydrogen at respectively 250° C., 300° C., 400° C. and 500° C. The supported catalysts thus reduced are then tested for their activity in the conversion of benzene under the following conditions:

| operation conditions: | |
|---|---|
| reaction temperature | 120° C. |
| reaction pressure | 8 atm |
| liquid hourly space velocity | 4 v/v/hr |
| C$_6$H$_6$/H$_2$ mole ratio | 1/6 mole/mole |

The result of the test is summarized in table 2 which shows that the best activity is obtained when the supported catalyst was reduced at about 300° C.

TABLE 2

The effect of the temperature at which the support catalyst is reduced on the activity of 2%Ni/TiO$_2$—ZrO$_2$ (1/1, 500° C.) catalyst

| reduction temperature, °C. | conversion, % |
|---|---|
| 250 | 50 |
| 300 | 67 |
| 400 | 35 |
| 500 | 5 |

EXAMPLE 3

The effect of the composition of the support on the activity of the supported catalyst Starting with solutions of titanium chloride (TiCl$_4$) and of zirconium chloride (ZrCl$_4$) in anhydrous ethanol, co-precipitate the hydroxides of Ti/Zr in a mole ratio of respectively 100/0, 99/10, 75/25, 50/50, 25/75, 10/90, 0/100 are obtained as the materials for support by the treatment with excess aqueous ammonia solution. After working up the seven co-precipitates in a manner similar in example 1, they are calcined at 550° C. for 2 hours and then impregnated with an aqueous solution of nickel nitrate such that the impregnated materials contain 2% by weight of metal nickel calculated on the dried basis. The impregnated materials are dried at 90° C. and then tested for their activities respectively in a reactor under the same reduction conditions and the reaction conditions are as follows:

| reduction temperature | 300° C. |
|---|---|
| reduction time | 2 hours |
| reaction temperature | 120° C. |
| reaction pressure | 8 atm |
| liquid hourly space velocity | 4 v/v/hr |
| C$_6$H$_6$/H$_2$ mole ratio | 1/6 mole/mole |

The result of the test is summarized in Table 3 which shows that a better activity can be obtained for the support in which the atomic ratio of Ti/Zr ranges from 3/1 to 1/3.

TABLE 3

The effect of the support composition on the activity of the supported catalyst 2%Ni/TiO$_2$—ZrO$_2$)

| atomic ratio of Ti/Zr | conversion, % |
|---|---|
| 100/0 | 72 |
| 90/10 | 74 |
| 75/25 | 76 |
| 50/50 | 84 |
| 25/75 | 78 |
| 10/90 | 65 |
| 0/100 | 56 |

EXAMPLE 4

Change in the activity of the supported catalyst obtained by supporting with different amounts of metal on the supports which was calcined at different temperature Starting with solutions of titanium chloride (TiCl$_4$) and of zirconium chloride (ZrCl$_4$) in anhydrous ethanol, a coprecipitate of the hydroxide of Ti/Zr in a mole ratio of 1/1 is obtained as the material for support by the treatment with excess ammonia solution. After working up the co-precipitate in a manner similar in example 1, the support is divided into four equal portions which are calcined at 450° C., 550° C., 650° C. and 750° C. respectively for 2 hours. Each portion of supports is further subdivided into several equal parts which are then impregnated separately with unequal amount of nickel nitrate solutions of the same concentration so as to obtain supported catalysts in which the amounts of nickel are different with one another. The supported catalyst thus obtained are compared for activity with respect to the pre-treatment condition and the reaction conditions are as follows:

| calcination temperature of catalyst | 90° C. |
|---|---|
| reduction temperature | 300+ C. |
| reduction time | 2 hours |
| reaction temperature | 100° C. |
| reaction pressure | 6 atm |
| liquid hourly space velocity | 6 v/v/hr |
| C$_6$H$_6$/H$_2$ mole ratio | 1/9 mole/mole |

The result is summarized in Table 4 which shows that the supported catalysts display better activity when the supports thereof have been calcined at 450° C. to 650° C. Meanwhile, in preparing the supports the surface area of the supports is varied with calcination temperature which also results in the variation of the best nickel content. The result is summarized in Table 5.

TABLE 4

Change in the activity of the supported catalysts obtained by supporting with different amounts of metal supports calcined at different temperature (expressed by conversion, %) wherein the supports used are TiO$_2$/ZrO$_2$ = 1/1

| temperature at which supports are calcined (°C.) | nickel amounts on the supports' |   |   |   |   |   |   |   |   |
|---|---|---|---|---|---|---|---|---|---|
| | 2 | 4 | 6 | 8 | 10 | 12 | 14 | 16 | 18 |
| 450 | — | — | 60 | 72 | 85 | 95 | 98 | 93 | 68 |
| 550 | — | — | 66 | 76 | 87 | 91 | 91 | 83 | 62 |
| 650 | 43 | 65 | 77 | 81 | 72 | 59 | — | — | — |
| 750 | 14 | 32 | 42 | 45 | 44 | 36 | — | — | — |

TABLE 5

The relationship between the surface area of the supports and the optimal supported metal content wherein the metal content is expressed by weight % and the supports used are TiO$_2$/ZrO$_2$ = 1/1

| surface area of the support (m$^2$/g) | calcination temperature, °C. | | | |
|---|---|---|---|---|
| | 450 | 550 | 650 | 750 |
| 275 | 14.5 | — | — | — |
| 240 | — | 12.5 | — | — |
| 130 | — | — | 8.2 | — |
| 55 | — | — | — | 7.9 |

The supported nickel catalyst of this application prepared by supporting nickel catalyst on mixed metal oxide of TiO$_2$/ZrO$_2$ as support is much superior to the conventional supported nickel catalyst in which alumina or diatomaceous earth is used as support with respect to the performance in converting benzene into cyclohexane, which may be confirmed by way of the following three reference examples:

REFERENCE EXAMPLE 1

The comparison of the activity of the supported catalysts in which TiO$_2$/ZrO$_2$, alumina and diatomaceous earth are used as supports respectively

TABLE 6 operational conditions:
reaction temperature: 100°°C. liquid hourly space velocity; 6 v/v/hr,
reaction pressure: 6 atms;

| type of catalyst | conversion rate of benzene |
|---|---|
| 2%Ni/Al$_2$O$_3$ | 15 |
| 2%Ni/SiO$_2$ | 11 |
| 2%Ni/TiO$_2$—ZrO$_2$ (1/1,650° C.) | 43 |

Table 6 shows that the supported catalyst of the present invention actually gets improved over the conventional supported catalysts in the hydrogenation of benzene.

REFERENCE EXAMPLE 2

Comparison of the supported catalyst with the commercially available catalysts with respect to activity

TABLE 7

| operation conditions: | |
|---|---|
| reaction temperature | 100° C. |
| liquid hourly space velocity | 6 v/v/hr |
| reaction pressure | 6 atm |
| C$_6$H$_6$/H$_2$ mole ratio | 1/9 mole/mole |
| type of catalyst | conversion, % |
| commercially available catalyst A | 93 |
| commercially available catalyst B | 85 |
| 15%Ni/TiO$_2$—ZrO$_2$ (1/1,450° C.) of the present invention | 98 |

In above table 7 commercially available catalyst A comprises 10% by weight of Ni on Al$_2$O$_3$, while commercially available catalyst B comprises raney nickel as main ingredient. Table 2 shows that under mild operation condition the supported catalyst of the present invention is more active than those catalyst currently used is the industry.

REFERENCE EXAMPLE 3

Measurement of the activity of the catalysts after long-time performance test with different feed composition

TABLE 8

| operation conditions: | |
|---|---|
| reaction temperature | 150° C. |
| liquid hourly space velocity | 6 v/v/hr |
| reaction pressure | 20 atm |
| C$_6$H$_6$/H$_2$ mole ratio | 1/7 mole/mole |
| testing period | 120 hour |

| | conversion of benzene after 120 hrs, % | |
|---|---|---|
| type of catalyst | benzene: 100% cyclohexane: 0% | benzene: 13% cyclohexane: 87% |
| 14%Ni/TiO$_2$—ZrO$_2$ (1/1, 450° C.) of the present invention | 99.80 | 99.96 |
| commercially available catalyst A | 99.75 | 99.92 |

Table 8 shows that after being long-time used (120 hours) under more severe operation conditions the supported catalyst of the present invention is superior to the conventionally available catalyst formerly used in the industry with respect to activity irrespective as to whether benzene is used alone or the mixture of benzene and cyclohexane is used as feed.

What we claimed is:

1. A process for converting benzene to cyclohexane by hydrogenation over a supported nickel catalyst comprising the steps of:
   mixing together and precipitating solutions of titanium compounds and zirconium compounds wherein said compounds are present in a atomic ratio of 25 Ti/75 Zr to 75 Ti/25 Zr;
   calcining said mixture at a temperature between 450° C. and 750° C. to produce a support;
   impregnating the surface of said support with a solution of nickel salt such that the nickel content is 2-18 weight percent based on the supported catalyst;
   calcining the resulting support at a temperature below 150° C.;
   reducing the supported catalyst at 250°-350° C.; and
   hydrogenating benzene to cyclohexane in a gas phase reaction by passing said benzene over said catalyst.

2. The process according to claim 1 wherein benzene or a mixture of benzene and cyclohexane is used as a feed.

3. The process according to claim 1 wherein the said hydrogenation is carried out under the conditions as follows:

| reaction temperature | 90-250° C. |
|---|---|
| reaction pressure | 5-30 atm |
| liquid hourly space velocity | 2-12 v/v/hr |
| C$_6$H$_6$/H$_2$ mole ratio | 1/3-20 mole/mole |

4. A process according to claim 1 wherein the atomic ratio of titanium to zirconium is 1:1.

5. A process according to claim 1 wherein said mixture is calcined at a temperature between 450° C. and 550° C.

6. A process according to claim 1 wherein the nickel content is 12-14 weight percent.

* * * * *